United States Patent [19]

Gross et al.

[11] Patent Number: 5,221,280
[45] Date of Patent: Jun. 22, 1993

[54] ELECTRIC HAIR REMOVAL DEVICE

[75] Inventors: Joseph Gross, Mazor; Zohar Avrahami, Rehovot, both of Israel

[73] Assignees: Product Development (ZGS) Ltd.; Elecsys Ltd., both of Petach Tikua, Israel

[21] Appl. No.: 773,841

[22] Filed: Oct. 9, 1991

Related U.S. Application Data

[63] Continuation-in-part of Ser. No. 528,395, May 25, 1990, abandoned.

[30] Foreign Application Priority Data

Jul. 24, 1991 [EP] European Pat. Off. ............ 91112411

[51] Int. Cl.⁵ .............................................. A61B 17/41
[52] U.S. Cl. ......................................... 606/36; 606/43
[58] Field of Search ...................................... 606/36, 43

[56] References Cited

U.S. PATENT DOCUMENTS

| 3,054,405 | 9/1962 | Tapper | 606/36 X |
| 4,033,350 | 7/1977 | Hoshi | 606/43 |
| 4,174,714 | 11/1979 | Mehl | 606/43 |
| 4,274,413 | 6/1981 | Hahn et al. | 606/43 X |

Primary Examiner—Lee S. Cohen
Attorney, Agent, or Firm—Benjamin J. Barish

[57] ABSTRACT

An electric hair removal device includes a holder to be hand-held by the user, and a pair of tweezer arms projecting from one end of the holder for gripping a hair to be removed from the skin in which the hair is growing. An electric power supply is actuated by a control device to automatically apply electric current to the hair while gripped by the tweezer arms and tensioned by the spring until the hair is plucked from the skin at which time the current automatically terminates. In one described embodiment, the control device is a tension sensor, and in another described embodiment it is a displacement detector.

20 Claims, 4 Drawing Sheets

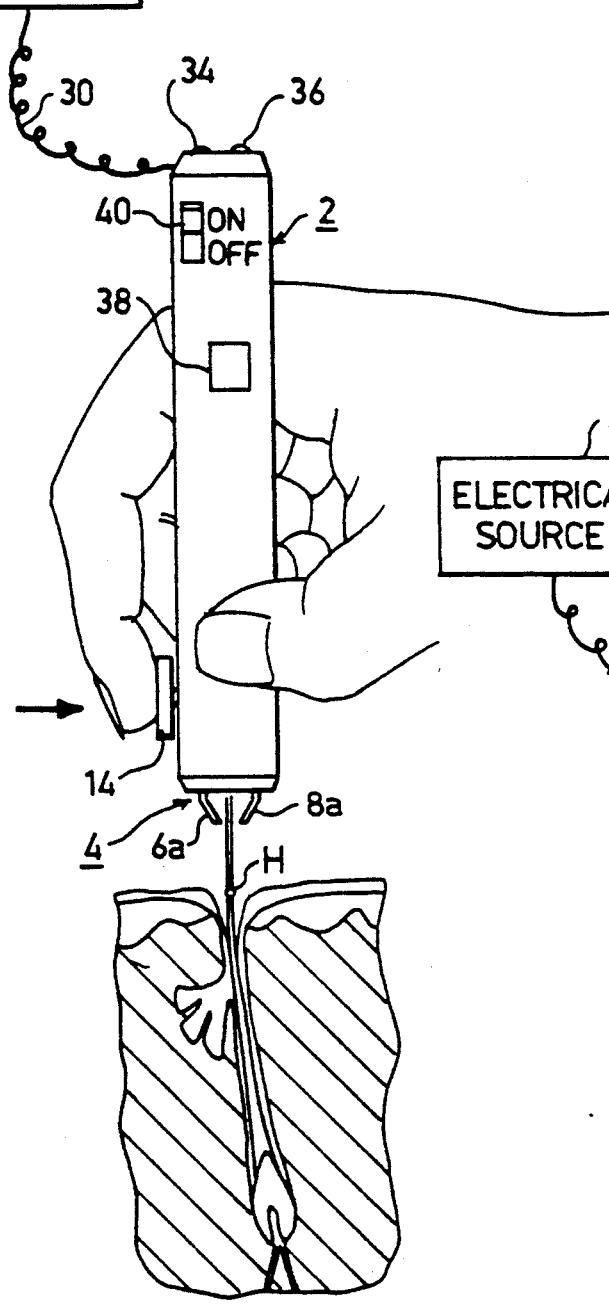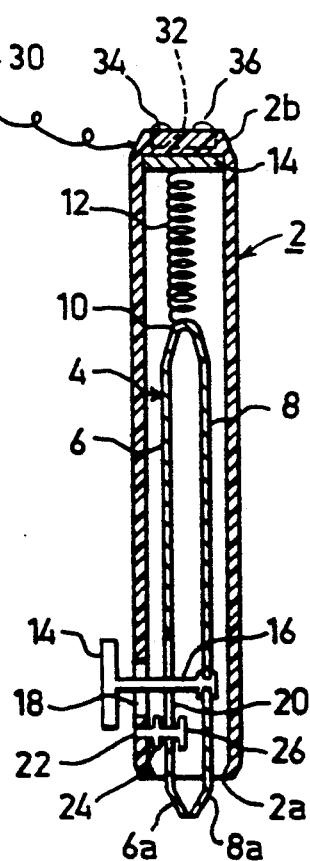

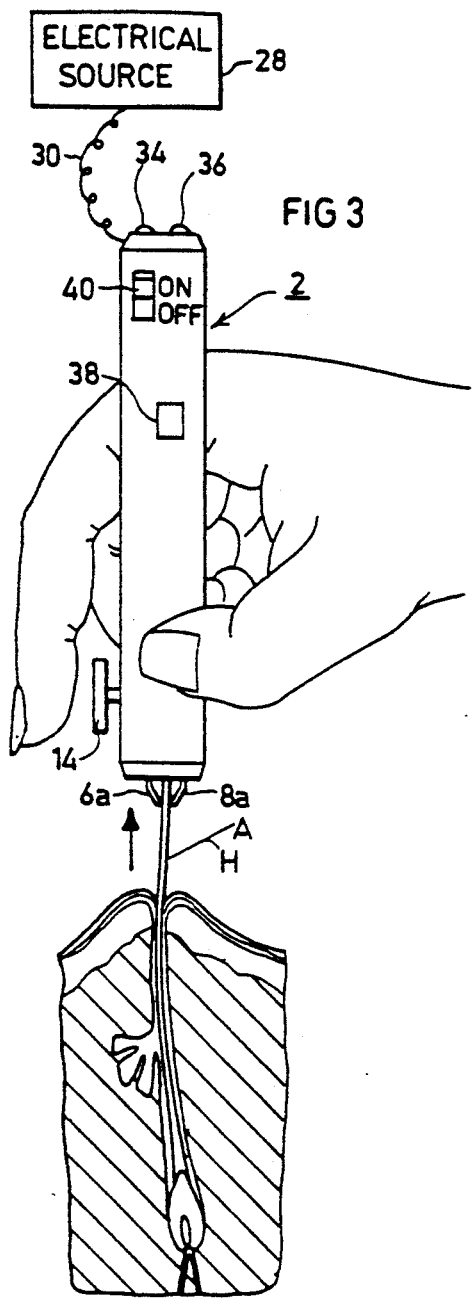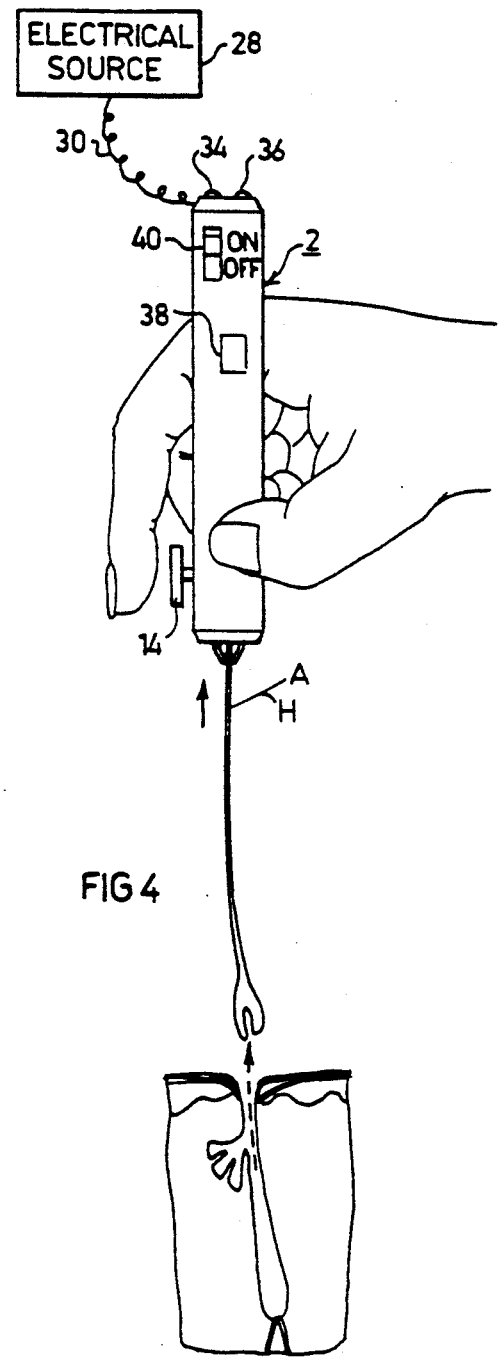

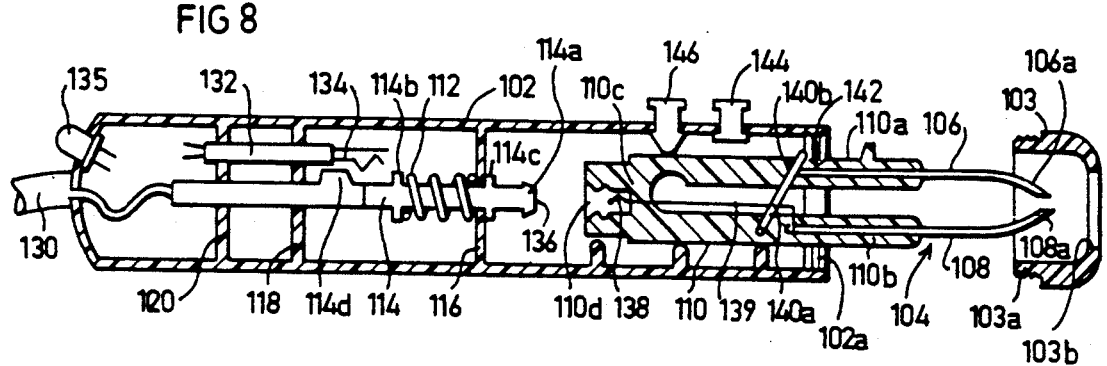
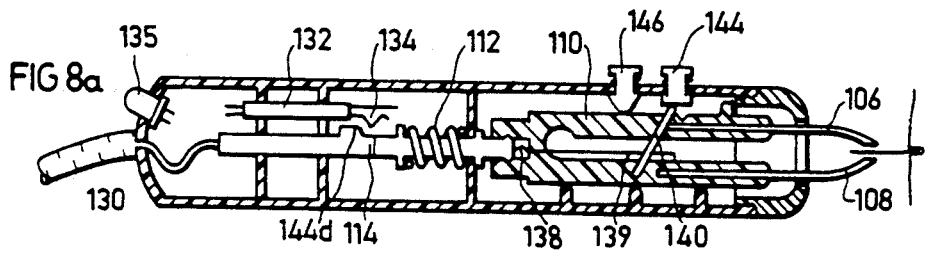
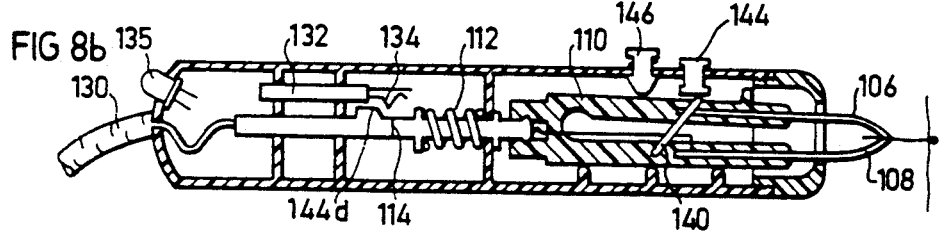
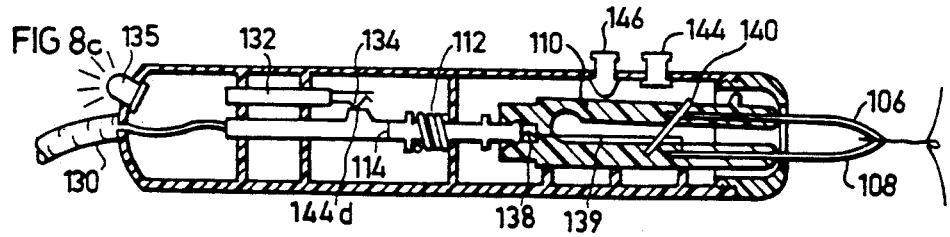
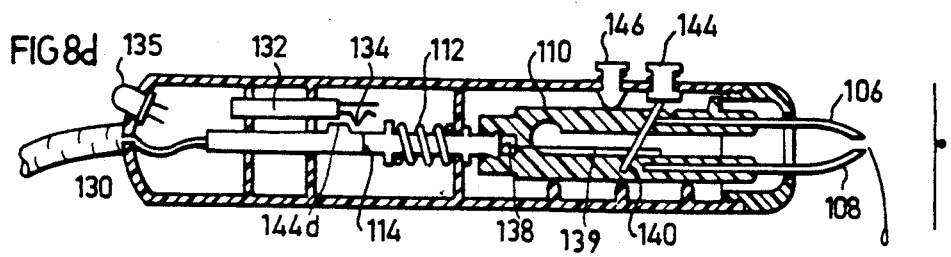

ELECTRIC HAIR REMOVAL DEVICE

RELATED APPLICATION

The present application is a continuation-in-part of our U.S. patent application Ser. No. 07/528,395, filed May 25, 1990, which application is abandoned.

FIELD AND BACKGROUND OF THE INVENTION

The present invention relates to hair removal devices, and particularly to an electric device for removing unwanted hair in a permanent manner.

One type of electrical device for the permanent removal of unwanted hair employs a needle which is inserted into the follicle adjacent the hair and receives high frequency electric current to destroy the hair producing papilla area; such devices, however, can be extremely irritating to the skin. Another type of device uses an electrically-charged tweezer which grips the hair and receives high frequency electric current. Examples of this type of device are described in U.S. Pat. Nos. 1,071,978, 2,894,512, 3,999,552 and 4,174,713. While the latter type of device avoids the skin irritation problem caused by needles, it can cause severe skin burns if the tweezer tip is brought too close to the skin surface when the high frequency electric current is applied.

OBJECTS AND BRIEF SUMMARY OF THE INVENTION

An object of the present invention is to provide an electric hair removal device of the tweezer-type but minimizing the danger of burning skin tissue by close proximity of the tweezer tip to the skin.

According to the present invention, there is provided an electric hair removal device for removing hairs from a user's skin comprising: a holder to be hand-held by the user; a pair of tweezer arms mounted to the holder and projecting from one end thereof for gripping a hair to be removed from the skin in which the hair is growing; an electric power supply connected to the tweezer arms for applying electric current to the hair gripped by the tweezer arms; and electric control means for actuating the electric power supply to apply electric current to the hair while gripped by the tweezer arms for automatically turning-off the electrical current to the tweezer arms when the hair is plucked from the skin.

Several embodiments of the invention are described below for purposes of example.

In one described embodiment, the electric control means comprises a tension sensor for automatically applying electric current to the tweezer arms when the tensile force applied to the hair, while gripped by the arms for plucking the hair from the skin, rises to a predetermined magnitude, and for automatically turning-off the electric current to the tweezer arms when the tensile force subsequently drops to a predetermined magnitude indicating that the hair has been plucked from the skin.

According to a second described embodiment, the device further includes a spring interposed between the holder and the tweezer arms and permitting the holder to be moved away from the skin while the tweezer arms grip the hair; in addition, the electric control means comprises a displacement detector for automatically applying electric current to the tweezer arms when the tweezer arms are displaced a predetermined magnitude with respect to the holder as permitted by the spring, and for automatically turning-off the electric current when the tweezer arms subsequently return to their initial position with respect to the holder indicating that the hair has been plucked.

Preferably, the first embodiment also includes a spring interposed between the holder and the tweezer arms permitting the holder to be moved away from the skin while the tweezer arms grip the hair.

According to further features in the above embodiments, the tweezer arms are normally spring-biassed to their closed positions gripping the hair and are movable to their open positions by a fingerpiece depressible by the user.

According to a third described embodiment, the tweezer arms are normally spring-biassed to their open positions for receiving a hair; the device further including a latch for latching the tweezer arms in their closed positions for gripping a hair, and manual operator means for selectively operating the latch to latch the tweezer arms to their closed positions or to release the latch to permit the tweezer arms to move to their open positions.

An electric hair removal device constructed in accordance with the foregoing features provides a number of important advantages over the tweezer-type devices previously used. Thus, the novel device enables the transmission of the electrical current while the tweezers are very close to the skin and yet minimizes the possibility of contact with the skin, or such close proximity, as might burn the skin tissue. In addition, the tensile force applied to the hair speeds up the plucking of the hair and also improves the transmission of the high frequency current to the papilla area, thereby reducing the time required for permanent removal of the hair.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates one form of electric hair removal device constructed in accordance with the present invention;

FIG. 2 is a sectional view more particularly illustrating the internal structure of the device of FIG. 1;

FIGS. 3 and 4 illustrate the manner of using the device of FIG. 1 for plucking hair;

FIG. 8 is a sectional view illustrating a third form of device constructed in accordance with the present invention; and FIGS. 8a-8d illustrate various stages in the use of the device of FIG. 8.

DESCRIPTION OF PREFERRED EMBODIMENTS

The Embodiment of FIGS. 1-5

Figure 5:
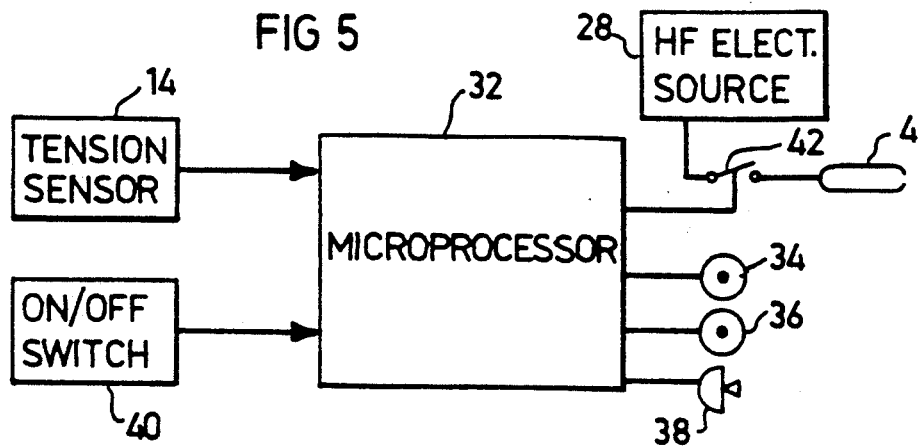
FIG. 5 is a block diagram illustrating the electric circuit in the device of FIG. 1.

FIGS. 1 and 2 illustrate an electric hair removal device including a holder 2 to be hand-held by the user, and a tweezers 4 disposed within the holder 2. Tweezers 4 include a pair of arms 6, 8 projecting through one end 2a of holder 2 where they terminate in inturned tips 6a, 8a for gripping the hair to be plucked. The two tweezer arms 6, 8 are joined at their opposite ends by a U-bend juncture section 10.

The juncture section 10 of tweezers 4 is mounted to the closed end 2b of holder 2 by means of a helical spring 12 and a tension sensor 14, such as a piezoelectric device, a strain gage, or the like.

Holder 2 is of a suitable insulating material and is of cylindrical configuration open at one end 2a and closed at the opposite end 2b. Tweezers 4 are made of metal, as is spring 12.

Tweezers 4 are biassed to their closed condition, wherein their tips 6a, 8a engage each other so as to firmly grip a hair when one is received between them. The two tweezer arms 6, 8 are manually moved to their open position in order to receive a hair between them by manually depressing a fingerpiece 14. As shown particularly in FIG. 2, fingerpiece 14 is connected to one end of a pin 16 which passes through an opening 18 in holder 2, and another opening 20 in tweezer arm 6, the opposite end of the pin being secured to the other tweezer arm 8. Thus, when fingerpiece 14 is depressed, tweezer arm 8 is moved away from tweezer arm 6. Tweezer arm 6 is in turn restrained against movement with tweezer arm 8 by means of another pin 22 secured at one end to holder 6 and having, at its opposite end, a pair of shoulders 24, 26 straddling the opposite sides of tweezer arm 6.

As will be described more particularly below, the high-frequency electric source 28 does not apply electric current to the tweezer arms 4, 6, until the tweezer arms have gripped the hair to be removed and the holder 2 has been moved outwardly with respect to the tweezer arms so as to apply tension to the hair. When the tensile force applied to the hair rises to a predetermined magnitude, the electric source is automatically turned on by the tension sensor 14; and when the tensile force subseqently drops to a predetermined low magnitude, indicating that the hair has been plucked, the elecric source is automatically turned off.

The tweezers 4 are connected to an electric source 28 via a cable 30 and a control circuit 32, such as a microprocessor, housed within the closed end 2b of holder 2. Holder 2 further includes two visual indicators 34, 36, an audio indicator 38, and a manual on/off switch 40. Visual indicator 34, which may be a green light source, is energized when the manual switch 40 is in its on-position to indicate that the device is ready for use; visual indicator 36, which may be a red light source, is energized to indicate when the electric source 28 has been actuated to apply electric current to the tweezers 4; and indicator 38, preferably an audio signal, provides a "beep" when the hair has been plucked by the tweezer arms from the skin.

The operation of the device will now be described particularly with reference to FIGS. 1, 3 and 4, and the block diagram of FIG. 5.

The holder 2 is held by the user's hand, as shown in FIG. 1, and manual switch 40 is turned to its on position, thereby placing the device in its Ready-state, which is indicated by the energization of the green-light 34. In this Ready-state, the two tweezer arms 6, 8 are biassed to their closed positions; electric source 28 is not energized, and therefore no current is applied between the two tweezer arms.

When a hair is to be removed, the user depresses fingerpiece 14, which causes tweezer arm 8 to open with respect to tweezer arm 6, thereby enabling the two tweezer arms to straddle a hair, (FIG. 1.). Fingerpiece 14 is then released, whereupon the two tweezer arms 6, 8 close and firmly grip the hair between them. The user then moves holder 2 away from the skin (FIG. 3); this is permitted by the stretching of spring 12, which spring also applies a tensile force to the hair gripped by the tweezer arms. The tensile force increases in magnitude as holder 2 is moved further away from the skin, and when the tensile force has risen to a predetermined magnitude, as sensed by tension sensor 14, microprocessor 32 is controlled to actuate a switch 42 (FIG. 5) between the electric source 28 and the tweezers 4 to apply high frequency electric current to the tweezer arms and thereby to the hair gripped by them.

This electric current destroys the papilla area at the base of the hair shaft resulting in the hair being plucked from the skin. As soon as the hair is thus plucked from the skin, the tensile force drops. When this occurs as sensed by the tension sensor 14, it causes the microprocessor 32 to reopen the switch 42 between the electrical source 28 and the tweezers, thereby terminating the supply of electric current to the tweezers.

The Red-light 36 is energized when the electric source applies, via the tweezer arms, high-frequency electric current to the hair gripped beween the tweezer arms, and the audio indicator 38 is energized to produce a "beep" signal when the hair has been plucked and the electric source deenergized, thereby signalling the user that the device may be used for removing another unwanted hair.

Since the electric source 28 is not energized until a predetermined tensile force has been applied to the hair to be removed, the device can be used for gripping the hair very close to the skin with a minimum danger of burning the skin. In addition, the application of the electric current to the hair while under tension more effectively transmits the electric current to the papilla area and also hastens the plucking action, thereby substantially reducing the time for removing an unwanted hair. Further, since the electric sources automatically denergize when a hair has been plucked, the device consumes a mimimum amount of electric power.

Figure 6:
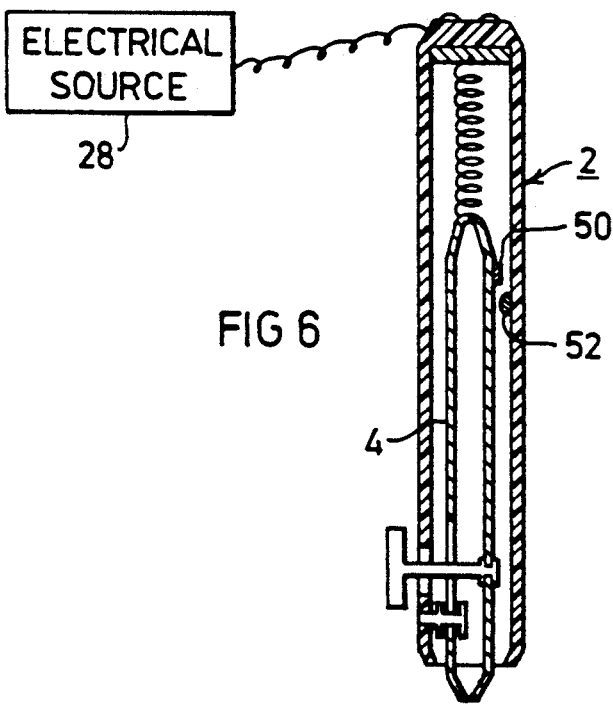
FIG. 6 is a sectional view illustrating a second form of device constructed in accordance with the present invention.
Figure 7:
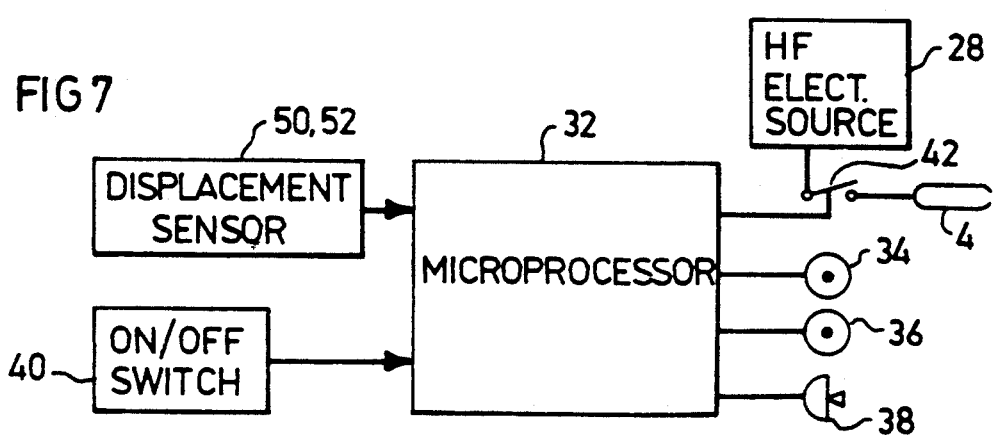
FIG. 7 illustrates the electric circuit of the device of FIG. 6.

The Embodiment of FIGS. 6 and 7

FIGS. 6 and 7, corresponding to FIGS. 2 and 5, respectively, illustrate a variation in the construction of the electric hair removal device. Thus, instead of using a tension sensor 14 for automatically controlling the electric source, the modified construction illustrated in FIG. 6 uses instead a displacement sensor measuring the displacement of the holder 2 with respect to the tweezers 4 when the tweezers have gripped the hair to be removed and the holder is moved outwardly to apply a tensile force to the hair.

The displacement sensor illustrated in FIG. 6 comprises an electric contact 50 on one of the arms of the tweezers 4, cooperable with an electric contact 52 on the holder 2. Thus, when the holder is moved outwardly while the tweezers grip and apply tension to the hair, spring 12 is stretched, as described above with respect to FIGS. 1-5, thereby moving electric contact 52 on the holder 2 towards electric contact 50 on the tweezers 4; and when the two contacts engage, they energize the electric source 28 to apply electric current via the tweezer arms to the hair gripped by them.

Contacts 50, 52 also detect the instant the hair is plucked, at which time these contacts automatically deenergize the electric source.

The Embodiment of FIG. 8

FIG. 8 illustrates another electric hair removal device including a holder 102 and a tweezers 104 including a pair of arms 106, 108 projecting through one end of the holder for gripping the hair to be plucked. One end of holder 102 is closed by an end cap 103 formed with external threads 103a receivable in internal threads 102a of the holder. End cap 103 is further formed with an opening 103b through which the inturned tips 106a, 108a of the two tweezer arms 106, 108 project. The two tweezer arms 106, 108 are carried by a plastic mounting member 110 having a pair of legs 110a, 110b each carrying one of the tweezer arms, and an elastic juncture 110c at the opposite end of the mounting member.

Mounting member 110, and its tweezer arms 106, 108, are spring-urged to a retracted position within holder 102 by a coiled spring 112 received over a stem 114 extending through openings formed in internal walls 116, 118 and 120 of holder 102. Stem 114 is formed with an enlarged head 114a received within a socket 110d in the body member 110.

The coiled spring 112 is interposed between an annular shoulder 114b in stem 114 and internal wall 116 of the holder 102. Stem 114 is formed with an additional annular shoulder 114c on the opposite side of wall 116 to limit the normal position of the stem.

Electric current is supplied to the tweezer arms 106, 108 via an electric cord 130, an electric switch 132 fixed between the internal walls 118, 120 of the holder 102, an electric contact 136 at the end of stem 114 engaging an electric contact 138 carried by mounting member 110, and a conductor 139 from contact 138 to one (or both) of the metal tweezer arms 106, 108. Electric switch 132 includes an actuator 134 in alignment with a projection 114d carried by stem 114. The electric switch 132 thus controls the electrical current supplied to the tweezer arms 106, 108 in accordance with the position of stem 114. Switch 132 also controls the electric current supplied to an LED 135.

The two legs 110a, 110b of mounting member 110 for the tweezer arms 106, 108 are normally spring-urged to the open condition of the tweezer arms by the elasticity of juncture 110c of the mounting member. The two legs 110a, 110b, however, may be latched in a closed position by a latching element 140. Latching element 140 includes a pair of parallel legs (one being shown at 140a) pivotally mounted to leg 110b of mounting member 110. The two legs of latching element 140 are joined at their opposite ends by a web section 140b which is receivable within a recess 142 for latching the two tweezer arms in their closed positions. The two legs 110a, 110b may be latched by latching member 140 to the closed positions of their respective tweezer arms 106, 108 by depressing button 144 carried by holder 102 normally overlying the web portion 140b of latching member 140, as shown in FIG. 8a. The two tweezer arms 106, 108 may be moved to their released position by depressing another button 146 overlying leg 110a of the mounting member 110.

FIGS. 8a–8d illustrate the various stages in the use of the tweezer of FIG. 8.

Thus, in its normal condition, the two tweezer arms 106, 108 are spring biassed to their open positions by the elasticity of juncture 110c of their mounting member 110. Thus, as shown in FIG. 8a, the open tweezer arms may be manipulated so as to receive a hair to be plucked. As soon as they receive such a hair, key 144 is depressed. This moves the mounting member leg 110b towards leg 110a, and at the same time moves the web portion 140b of latching member 140 into recess 142 formed in leg 110b, thereby latching the two legs to the position illustrated in FIG. 8b wherein their tweezer arms 106, 108 grip the hair.

The user now moves the holder 102 away from the skin, thereby applying tension to the hair to be plucked, and displacing the tweezer arms 106, 108 against the action of spring 112. When sufficient tension has been applied, projection 114c carried by stem 114, fixed to the tweezer arm mounting member 110, engages the switch actuator 134 to actuate the electrical switch 132, and thereby to supply electric current to the tweezer arms 106, 108, and also to the LED 135 (FIG. 8c).

When the hair has been plucked, spring 112 automatically retracts the tweezer arms 106, 108 within the holder 102, thereby also causing projection 114c of stem 114 to disengage from actuator 134 of the electrical switch 132, thereby interrupting the electrical current supplied to the tweezer arms.

Key 146 is now manually depressed, moving mounting member leg 110b towards leg 110a, which releases latching member 140 from recess 142. The two tweezer arms 106, 108 return to their normal open condition by the elasticity of mounting member juncture 110c, thereby releasing the hair from the grip between the two tweezer arms (FIG. 8d).

In all the above-described embodiments, particularly good results were obtained where the operating voltage applied to the tweezer arms was 70–150 volts, preferably about 120 volts; and the operating frequency was 20–30 MHz, preferably about 27 MHz. In addition, the tweezer arms preferably include interchangeable tips.

While the invention has been described with respect to three preferred embodiments, it will be appreciated that many variations may be made. For example, instead of automatically denergizing the electric source in response to the plucking of a hair, the electric source may be deenergized only after the elapse of a fixed time interval sufficient to destroy the hair. In addition, where a tension sensor is used as described above with respect to FIGS. 1–5, the provision of the helical spring 12 is not essential since tension, and not displacement, is sensed in this embodiment.

Many other variations, modifications and applications of the invention will be apparent.

What is claimed is:

1. An electric hair removal device for removing hairs from a user's skin, comprising:
   a holder to be hand-held by the user;
   a pair of tweezer arms mounted to said holder and projecting from one end thereof for gripping a hair to be removed from the skin;
   an electric power supply connected to said tweezer arms for applying electric current to the hair gripped by said tweezer arms;
   and electric control means for supplying electric current to said hair while gripped by said tweezer arms and for automatically turning-off the electrical current to the tweezer arms when the hair is plucked from the skin.

2. The device according to claim 1, wherein said electric control means comprises tensile force sensor means for automatically applying electric current to said tweezer arms when a tensile force applied to said hair, while gripped by said arms for plucking the hair from the skin, rises to a predetermined magnitude, and for automatically turning-off the electric current to the tweezer arms when the tensile force subsequently drops to a predetermined magnitude indicating that the hair has been plucked from the skin.

3. The device according to claim 1, wherein the device further includes a spring interposed between said holder and tweezer arms and permitting the holder to be moved away from the skin while said tweezer arms grip the hair;

and wherein said electric control means comprises displacement detector means for automatically applying electric current to said tweezer arms when the tweezer arms are displaced a predetermined magnitude with respect to the holder as permitted by said spring, and for automatically turning-off the electric current when the tweezer arms subsequently return to their initial position with respect to the holder indicating that the hair has been plucked.

4. The device according to claim 3, wherein said tweezer arms are carried by a mounting member having first and second legs each carrying one of said tweezer arms at one of their ends and joined together at their opposite ends by an elastic juncture;

said spring being interposed between a stem fixed to said juncture of the mounting member and a fixed surface of said holder, to permit the tweezer arms to move from a normal position with respect to the holder for receiving and gripping the hair, to a displaced position with respect to the holder when the holder is moved away from the skin while the tweezer arms grip the hair.

5. The device according to claim 4, wherein said electrical control means comprises an electrical switch fixed within said holder and engageable by a projection carried by said stem to supply electric current to the tweezer arms when the tweezer arms are axially displaced from their normal positions, and to turn-off the electric current to the tweezer arms when the tweezer arms are returned to their normal positions.

6. The device according to claim 1, wherein said tweezer arms include a fingerpiece depressible by the user, said tweezer arms being normally spring-biassed to their closed positions gripping the hair and being movable to their open positions by said fingerpiece when depressed by the user.

7. The device according to claim 1, wherein said tweezer arms are normally spring-biassed to their open positions for receiving a hair;

said device further including a latch for latching the tweezer arms in their closed positions for gripping a hair, and manual operator means for selectively operating the latch to latch the tweezer arms to their closed positions or to release the latch to permit the tweezer arms to move to their open positions.

8. The device according to claim 7, wherein said tweezer arms are normally biassed to their open positions by a mounting member having first and second legs each carrying one of said tweezer arms at one of their ends, and joined together at their opposite ends by an elastic juncture.

9. The device according to claim 8, wherein said latch comprises a first end pivotally mounted to said first leg, and a second end receivable within a groove in said second leg for latching the two tweezer arms in their closed positions.

10. The device according to claim 9, wherein said manual operator means comprises:
a first depressible key mounted to said holder in alignment with said second end of the latch for moving same into said groove of said second leg;
and a second depressible key mounted to said holder in alignment with said second leg for moving same towards the first leg, and thereby for releasing said second end of the latch from said second leg.

11. The device according to claim 1, wherein said power supply supplies an operating voltage applied to the tweezer arms of 70–150 volts, at an operating frequency of 20–30 MHz.

12. An electric hair removal device for removing hairs from a user's skin, comprising:
a holder;
a pair of tweezer arms mounted to said holder and projecting from one end thereof for gripping a hair to be removed from the skin and for applying a tensile force to the hair for plucking the hair from the skin;
an electric power supply connected to said tweezer arms for applying electric current to the hair gripped by said tweezer arms;
and electric control means comprising tensile force sensor means for automatically applying electric current to said tweezer arms when said tensile force rises to a predetermined magnitude, and for automatically turning-off the electric current to the tweezer arms when the tensile force subsequently drops to a predetermined magnitude indicating that the hair has been plucked from the skin.

13. The device according to claim 12, wherein said tweezer arms include a fingerpiece depressible by the user, said tweezer arms being normally spring-biassed to their closed positions gripping the hair and being movable to their open positions by said fingerpiece when depressed by the user.

14. The device according to claim 12, wherein said tweezer arms are normally spring-biassed to their open positions for receiving a hair; said device further including a latch for latching the tweezer arms in their closed positions for gripping a hair, and manual operator means for selectively operating the latch to latch the tweezer arms to their closed positions or to release the latch to permit the tweezer arms to move to their open positions.

15. The device according to claim 14, wherein said tweezer arms are normally biassed to their open positions by a mounting member having first and second legs each carrying one of said tweezer arms at one of their ends, and joined together at their opposite ends by an elastic juncture.

16. The device according to claim 15, wherein said latch comprises a first end pivotally mounted to said first leg, and a second end receivable within a groove in said second leg for latching the two tweezer arms in their closed positions.

17. The device according to claim 16, wherein said manual operator means comprises: a first depressible key mounted to said holder in alignment with said second end of the latch for moving same into said groove of said second leg; and a second depressible key mounted to said holder in alignment with said second leg for moving same towards the first leg, and thereby for releasing said second end of the latch from said second leg.

18. An electric hair removal device for removing hairs from a user's skin, comprising:

a holder;

a pair of tweezer arms mounted to said holder and projecting from one end thereof for gripping a hair to be removed from the skin and for applying a tensile force thereto for plucking the hair from the skin;

an electric power supply connected to said tweezer arms for applying electric current to the hair gripped by said tweezer arms;

a spring interposed between said holder and tweezer arms and permitting the holder to be moved away from the skin while said tweezer arms grip the hair;

and electric control means comprising displacement detector means for automatically applying electric current to said tweezer arms when the tweezer arms are displaced a predetermined magnitude with respect to the holder as permitted by said spring, and for automatically turning-off the electric current when the tweezer arms subsequently return to their initial position with respect to the holder indicating that the hair has been plucked.

19. The device according to claim 18, wherein said tweezer arms are carried by a mounting member having first and second legs each carrying one of said tweezer arms at one end of their ends and joined together at their opposite ends by an elastic juncture; said spring being interposed between a stem fixed to said juncture of the mounting member and a fixed surface of said holder, to permit the tweezer arms to move from a normal position with respect to the holder for receiving and gripping the hair, to a displaced position with respect to the holder when the holder is moved away from the skin while the tweezer arms grip the hair.

20. The device according to claim 19, wherein said electric control means comprises an electrical switch fixed within said holder and engageable by a projection carried by said stem to supply electric current to the tweezer arms when the tweezer arms are axially displaced from their normal positions, and to turn-off the electric current to the tweezer arms when the tweezer arms are returned to their normal positions.

* * * * *